United States Patent [19]

Scales

[11] 4,405,249
[45] Sep. 20, 1983

[54] DISPENSING APPARATUS AND METHOD

[75] Inventor: John T. Scales, Stanmore, England

[73] Assignee: National Research Development Corporation, London, England

[21] Appl. No.: 245,606

[22] Filed: Mar. 19, 1981

[30] Foreign Application Priority Data

Mar. 28, 1980 [GB] United Kingdom ............... 8010522

[51] Int. Cl.³ .............................................. B43K 5/06
[52] U.S. Cl. ...................................... 401/182; 401/176; 604/222; 128/92 G
[58] Field of Search .............. 401/171, 178, 176, 179, 401/182; 222/387, 391, 478, 386; 141/20.5, 23, 27, 29; 92/181 R, 181 P, 184; 425/87, 376 R; 604/218, 222; 128/92 R, 92 G, 218 P, 218 PA, 230, 265, 234

[56] References Cited

U.S. PATENT DOCUMENTS

| | | | |
|---|---|---|---|
| 33,637 | 11/1861 | Dungan | 222/387 |
| 665,013 | 1/1901 | Jones | 222/387 |
| 2,236,727 | 4/1941 | Dewees | 222/386 |
| 3,147,753 | 9/1964 | Nogier et al. | 128/218 P |
| 3,253,592 | 5/1966 | Von Pechmann | 222/386 X |
| 3,464,412 | 9/1969 | Schwartz | 222/386 X |
| 3,658,056 | 4/1972 | Huggler et al. | 3/1.912 X |
| 3,674,181 | 7/1972 | Marks et al. | 222/386 X |
| 3,905,521 | 9/1975 | Mead et al. | 128/218 PA X |
| 3,993,061 | 11/1976 | O'Leary | 128/234 X |
| 4,266,557 | 5/1981 | Merry | 128/218 P X |

FOREIGN PATENT DOCUMENTS

| | | |
|---|---|---|
| 276192 | 8/1927 | United Kingdom . |
| 277896 | 9/1927 | United Kingdom . |
| 354403 | 8/1931 | United Kingdom . |
| 748245 | 4/1956 | United Kingdom . |
| 901161 | 7/1962 | United Kingdom . |

Primary Examiner—Edgar S. Burr
Assistant Examiner—Charles A. Pearson
Attorney, Agent, or Firm—Cushman, Darby & Cushman

[57] ABSTRACT

A syringe, primarily for use with rapid hard setting viscous flowable material, has one or more passages in the piston whereby gas but not the viscous flowable material can escape to the rear of the piston.

7 Claims, 6 Drawing Figures

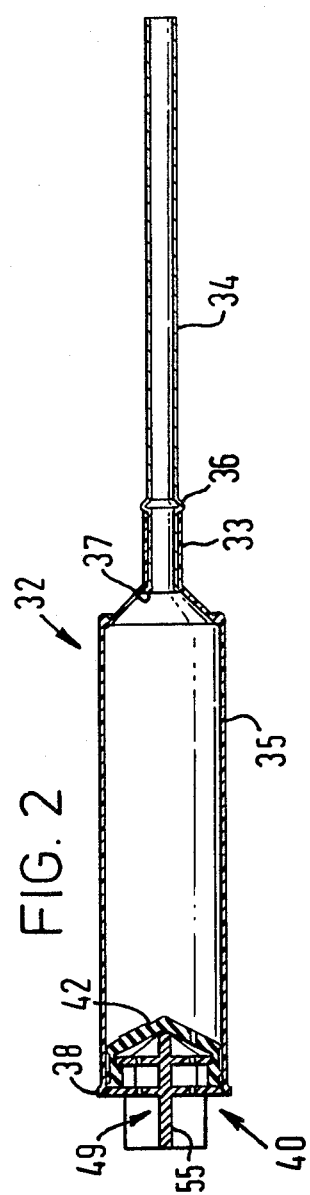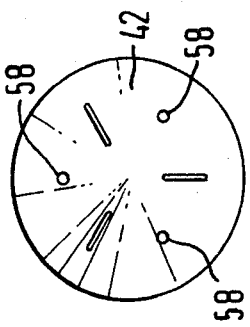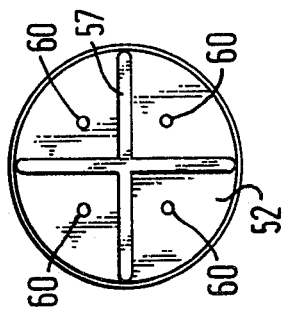

DISPENSING APPARATUS AND METHOD

The present invention relates to an apparatus for and method of dispensing a viscous material which is flowable under pressure and such apparatus will be referred to hereinafter as a syringe. The invention relates to a syringe for expressing the viscous flowable material by application of pressure, to an injection gun into which the syringe may be fitted, and to a method for delivering the viscous flowable material to a treatment site using the syringe. The invention is particularly applicable to expresssing bone cement, but is also of value for the expressing or ejection of other flowable materials which may be in the form of viscous liquids or pastes, for example, a curable resin composition.

Acrylic bone cements are used in surgery for cementing prostheses such as hip joints and knee joints into living bone. They are provided in two component form, one component being a powder which may consist of polymethyl methacrylate homopolymer or of a copolymer of methyl methacrylate and styrene, and the other component being liquid methyl metharylate. Such materials are currently available. When the two components are mixed together, they form a pourable mixture which changes after a relatively short time into a paste, which is the form in which it is applied to the treatment site, and which is then converted, again after a relatively short time, into a rigid material. Bone cements are expensive materials and they cure quickly once they are mixed, typically within a few minutes. There is therefore a requirement by the surgeon for an applicator into which he need put only the amount of bone cement which he intends to use, and which is simple and rapid to set up.

One possibility is to pour the cement into the body of a syringe and to express the cement by advancing the piston under mechanical pressure. However, in practice air will always be left between the piston and the charge of bone cement, especially where the syringe is only partly filled, and there is a problem of how to remove the air rapidly and effectively during assembly of the syringe. An attempt to solve the problem by providing a piston which fits in the syringe so that air can escape around its periphery would not be acceptable because during ejection of the bone cement, material would leak to the back face of the piston and would contaminate the injection gun which, unlike the syringe, is not a disposable item.

According to the present invention there is provided a syringe for dispensing a viscous material which is flowable under pressure, the syringe comprising a body having an internal bore with an outlet at one end of the bore and a piston for expressing viscous flowable material through the outlet by advancement of the piston towards the outlet and contact of the front face of the piston with the flowable material, wherein said front face has apertures therethrough which are of a size such as to allow passage of a gas but to substantially prevent passage of the viscous flowable material, and one or more forward chambers are defined within the piston into which said apertures debouch, and gas flow communication from said chambers to the rear of the piston, whereby gas but not flowable material passes to the rear of the piston during expression of the material through the outlet.

It is preferred that the piston includes successive wall components across the bore which provide successive barriers to unwanted passage of the flowable material rearwardly. In such a case a series of apertures may be provided through the succeeding components to allow communication from the front to the rear of the piston. However, it is preferred that the main barrier to unwanted rearward passage of material is provided by the front face of the piston which has apertures therethrough of a size such as to allow passage of a gas but to prevent or inhibit passage of a viscous flowable material.

Preferably the syringe is provided with a piston arranged so that portions thereof in sealing engagement with the wall of the bore are deformed radially outwards under load when the piston is in contact with the flowable material, whereby the effectiveness of the peripheral seal is increased. It is particularly preferred that the piston comprises a deformable cap, e.g. of rubber or other resilient material, which fits over the front end of a rigid plug, e.g. of polypropylene, said cap having one or more apertures therethrough which are of a size such as to allow passage of a gas but substantially to prevent passage of the viscous flowable material and said cap being deformable radially outwardly under load when the piston is in contact with the flowable material to sealingly engage the wall of the bore. The cap preferably is formed with a generally conical head, a skirt which fits onto the plug, and at least one radially expansible circumferential ring for sealing against the wall of the bore. The skirt is preferably formed of two circumferential rings spaced axially apart. The cap and the plug may together define one or more rearward chambers behind said forward chamber(s) and gas flow apertures in the plug communicate said forward chamber(s) with said rearward chamber(s). The plug may be formed with a first transverse apertured plate, a second transverse apertured plate behind the first and of larger diameter, and members extending from the front face of the first plate to support the head of the cap. A circumferential flange may be provided on the inner surface of the skirt which is entrapped between the first and second plates to fix the cap to the plug. Fins may extend from the rear end of the piston whose rear ends terminate in a common plane directed transversely of the piston.

The syringe may be formed with a neck projecting forwardly from a wall of the body and a delivery tube through which the flowable material is ejected may be secured within the neck in fluid communication with the interior of the syringe. The delivery tube may be of metal and may be swaged to define a collar which locates against the forward end of the neck and a flange projecting from the rear end of the delivery tube which locates against portions of the front wall of the syringe adjoining the neck so that the delivery tube is secured in a fixed longitudinal position relative to the syringe body.

The syringe body may be formed at its rear end with a radially projecting circumferential flange by means of which the syringe may be located within a barrel of an ejection gun as described below.

The front face of the piston may be formed with a plurality of apertures from 1.5 to 3.3 mm in diameter and preferably about 2.2 mm in diameter. The apertures may be formed at an intermediate radial position or they may be defined by slots in the circumference of the piston. Where the syringe has a plug formed with first and second plates as described above and a cap formed with apertures at an intermediate radial position, gas flow apertures are formed in the first and second plates having similar sizes to the apertures in the cap.

Where the syringe is required for medical purposes it is preferably sterile and is enclosed in packaging means such as plastics foil hermetically sealed or otherwise arranged so that the sterility of the syringe is preserved until it is required to be used.

From another aspect, the invention provides apparatus for ejection of a viscous liquid comprising a syringe as aforesaid located in a removable barrel of an injection gun having a trigger, a handle and an operating rod terminating in a plunger, successive strokes of the trigger towards the handle advancing the plunger so that it locates behind the piston and advances the piston to eject the flowable material. The barrel preferably has a shoulder against which the circumferential flange preferably provided at the rear of the syringe body abuts to locate the syringe in the barrel, and preferably the barrel fits in the injection gun by means of a bayonet fitting.

An embodiment of the invention will now be described by way of example only with reference to the accompanying drawings in which:

FIG. 2 is a view of the syringe in longitudinal section;

FIG. 3 is a front view of a plastics plug which supports the syringe piston assembly;

FIG. 5 is a front view of a piston cap of elastomeric material forming part of the syringe piston assembly.

Figure 1:
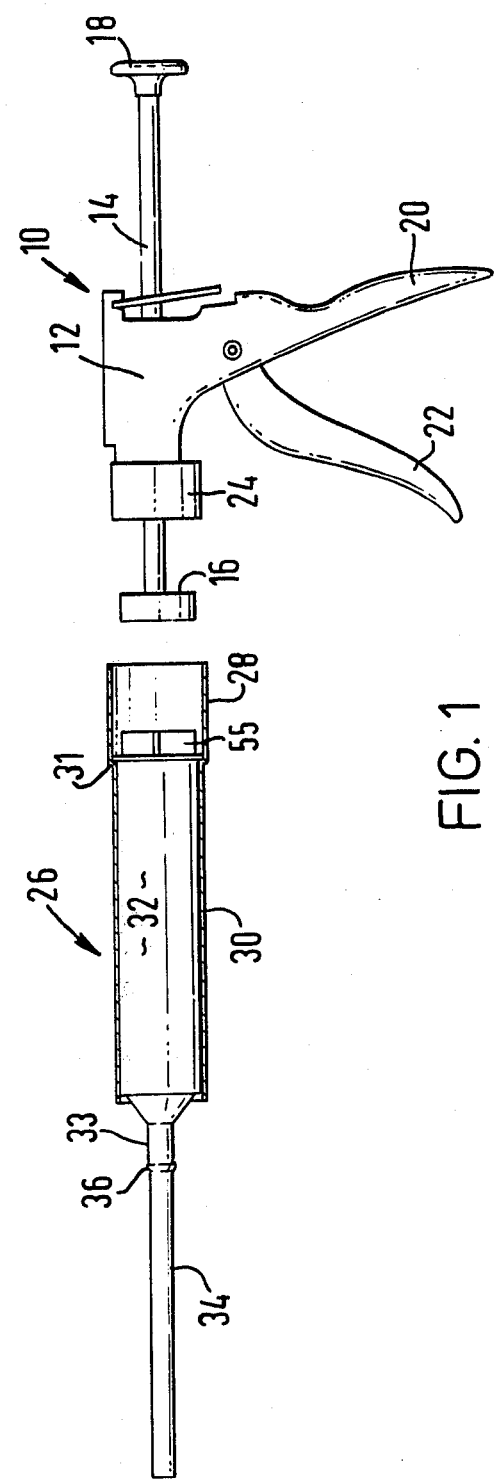
FIG. 1 is a side view of an injection gun and a barrel disassembled from the gun and shown in longitudinal section to reveal within it a disposable syringe.
Figure 6:
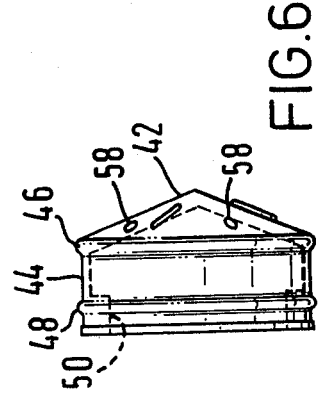
FIG. 6 is a side view of the piston cap of FIG. 5.
Figure 4:
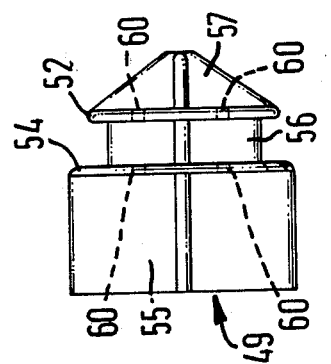
FIG. 4 is a side view of the plastics plug of FIG. 3.

In FIG. 1, which shows the general arrangement of a syringe, barrel and injection gun, a hand held ratchet gun 10 comprises a body 12 through which an operating rod 14 can be advanced by repeatedly squeezing a trigger 22 towards a handle 20. The trigger 22 is operatively connected to a mechanism known per se and including a ratchet, which mechanism is located within the body 12 and brings about the advance of the rod 14 in response to successive strokes of the trigger 22. The front end of the rod 14 is formed with a disc-shaped plunger 16 and the rear end of the rod 14 is provided with a knob 18 by means of which the rod 14 and plunger 16 can be reset to the beginning of their travel when required. The front of the body 12 is provided with a locking ring 24 formed with a radially projecting bayonet lug or lugs (not shown).

The ratchet gun is provided with a removable barrel 26 of rigid autoclavable material which may be a plastics material such as polypropylene formed with a shoulder 31 defining a front portion 30 of smaller diameter and a rear portion 28 of larger diameter. A disposable syringe 32 may be introduced into the barrel 26 from the rear end and may be slid forwardly within the front portion 30 in which it fits until it is located by abutment of an outwardly directed circumferential locating flange 38 (FIG. 2) with the shoulder 31. The larger diameter rear portion 28 of the barrel fits over the locking ring 24 and is formed with a notch or notches or cut-outs (not shown) corresponding to the bayonet lug(s) on the locking ring so that the barrel carrying the syringe can be secured to the ratchet gun.

In FIG. 2 the syringe 32 comprises a cylindrical body 35 of plastics material formed with a neck 33 projecting forwardly from a front wall thereof and with the locating flange 38 at the rear end thereof. A metal delivery tube 34 fits within the neck 33 and is located at the front end of the neck 33 by a collar 36 formed by swaging the tube 34 or by any other convenient means and is located at the rear end of the neck 33 by means of a swaged flange 37 so that the delivery tube 34 is held in a fixed position relative to the body 35. A piston 40 fits into the inner cylindrical space of the syringe body 35 and comprises a cap 42 of an elastomeric material such as rubber which fits over a plug 49 of rigid plastics material such as polypropylene. The plug 49 is formed with a front plate 52 and a rear plate 54 of slightly larger diameter each directed transversely as shown. Four generally rectangular rear fins 55 project from the back face of the plate 54 and the plates 52 and 54 are interconnected by intermediate fins 56 whose edges terminate within the periphery of the front plate 52 as shown. Four front fins 57 of triangular shape project from the front face of the plate 52. The cap 42 fits over the front end of the plug and comprises a generally conical head and a generally cylindrical skirt 44 formed with a front circumferential ring 46 and a rear circumferential ring 48. At the rear end of the skirt is formed an inwardly projecting locating flange 50. When the plug and the cap are fitted together the periphery of the front plate 52 and the triangular fins support the head of the cap and the locating flange 50 is entrapped within the space between the plates 52 and 54 as shown in FIG. 2 so that the cap is fixed to the plug. The cap is formed with relatively small through holes 58 disposed in a triangular pattern as shown, and the plates 52 and 54 are formed with relatively small through holes 60 disposed in a square pattern between the fins 56 as shown, whereby a gas flow path is established between the front and rear faces of the piston assembly 40.

The syringe is typically of about 170 cc capacity and is typically of 4 cms outside diameter and 16 cms in length, and the discharge nozzle is typically about 18 cms in length. The diameter of the through holes 58 and 60 is such that gas can flow readily through them but viscous liquids or pastes flow through them to a negligible degree, and they may be from 1.5 to 3 mm in diameter, and typically about 2.2 mm in diameter.

For medical use, e.g. when the material to be ejected is bone cement, the syringe which is normally a disposable item is sterilized and is preferably packaged in an air-tight plastics or metal foil, the pack being such as to retain the syringe in its sterile condition until it is required.

In use, about 50-150 ml of a curable viscous pourable material such as bone cement is introduced into the body 35 of a sterile syringe 32 so that it is approximately half full. The bone cement consists of a mixture of liquid monomethyl methacrylate and a methyl methacrylate polymer or copolymer with e.g. styrene in powder form, and suitable materials are available under the trade names CMW bone cement, Simplex C, Simplex P and Simplex P (Radioopaque). Within a relatively short period of time, the bone cement partially cures into a paste, which is in the form in which it is extruded to the required treatment site. As previously stated, the bone cement remains in a workable state for only a short time, so that it is important to be able to introduce the piston and assemble the injection gun quickly. After introduction of the bone cement, a sterile piston 40 is fitted into the rear end of the syringe and the syringe is introduced into the barrel 26 (which is not normally a disposable item, but which has been autoclaved beforehand to render it sterile). The end 28 of the barrel is then fitted to the control ring 24 and the trigger 22 is operated to bring the plunger 16 into contact with the fins 55, after which further strokes of the trigger 22 force the piston 40 forwardly into the syringe. During an initial portion of the travel of the piston 40 entrapped air escapes to the rear of the piston from the space between the charge of bone cement and the front of the piston through the apertures 58 and 60 so that the elastomeric piston can be brought into contact with the charge of bone cement with substantially complete removal of entrapped air. Further strokes of the trigger 22 cause paste-like bone cement to be extruded through the discharge nozzle 34, but owing to the relatively small size of the holes 58 and 60, bone cement does not reach the rear face of the piston. In particular the head 42 of the cap defines with the fins 57 and the plate 52 a set of first chambers within the piston 40 and the plates 52 and 54 together with fins 56 and the skirt 44 define a set of second chambers within the piston. Air can flow through holes 58 into the first chambers, through apertures 60 in plate 52 to the second chamber and thence through apertures 60 in plate 54 to the rear of the piston. If any bone cement flows through the holes 58 or the holes 60 in plate 52, it does so only slowly and remains in the first and second chambers without reaching the rear of the piston. Furthermore, when the conical head 42 of the cap contacts the charge of bone cement, the skirt 44 is compressed against the rear plate 54 of the plug whereby the skirt 44 bows radially outwards and the circumferential rings 46 and 48 are urged more tightly against the inner cylindrical surface of the syringe body 35 to prevent escape of bone cement around the periphery of the piston. Accordingly the bone cement can be injected at the intended site without any bone cement passing behind the piston to damage the ratchet gun 10 or barrel 26.

I claim:

1. A disposable syringe for use with a non-disposable injection gun for dispensing bone cement which is flowable under pressure comprising a body having an internal bore with an outlet at one end of the bore and a piston having a front face for expressing viscous flowable material through the outlet by advancement of the piston towards the outlet and contact at the front face of the piston with the flowable material and a rear face, wherein said front face is deformable and generally conically shaped with apertures therethrough which are of a size such as to allow passage of a gas but to substantially prevent passage to the viscous flowable material to said non-disposable injection gun, and one or more forward chambers are defined within the piston into which said apertures debouch, and gas flow communication from said chambers to the rear face of the piston, whereby gas but not flowable material passes to the rear face of the piston during expression of the material through the outlet, said piston because of its deformability and generally conical shape deforming radially outwardly under load to sealingly engage the wall of said bore.

2. A syringe according to claim 1 in which the piston comprises successive wall components across the bore to provide successive barriers to rearward passage of the flowable material.

3. A syringe according to claim 1 in which the piston comprises a rigid plug and a deformable cap over the front end of the plug, said cap constituting the said front face of the piston and being deformable radially outwardly under load to sealingly engage the wall of the bore.

4. A syringe according to claim 3 in which the cap has a generally conical head, a skirt which fits onto the plug and at least one radially expansible circumferential ring for sealing against the inner surface of the bore.

5. A syringe according to claim 3 wherein the cap and plug together define one or more rearward chambers behind said forward chambers and gas flow apertures in the plug communicate said forward chambers with said rearward chambers.

6. A syringe according to claim 5 wherein the plug is formed with a first transverse apertured plate, a second transverse apertured plate behind the first and of larger diameter and members extending forwardly from the front face of the first plate to support the head of the cap.

7. A disposable apparatus for use with a non-disposable injection gun for dispensing bone cement which is flowable under pressure comprising a syringe having a piston with a front and rear face located in a removable barrel of said injection gun having a trigger, a handle and an operating rod terminating in a plunger, successive strokes of the trigger towards the handle advancing the plunger so that it locates behind the piston to the syring and advances the piston to eject the flowable material from the syringe, wherein said front face is deformable and generally conically shaped with apertures therethrough which are of a size such as to allow passage of a gas but to substantially prevent passage of the viscous flowable material to said non-disposable injection gun, and one or more forward chambers are defined within the piston into which said apertures debouch, and gas flow communication from said chambers to the rear face of the piston, whereby gas but not flowable material passes to the rear face of the piston during expression of the material through the outlet, said piston because of its deformability and generally conical shape deforming radially outwardly under load to sealingly engage the wall of said bore.

* * * * *